Figure 3:
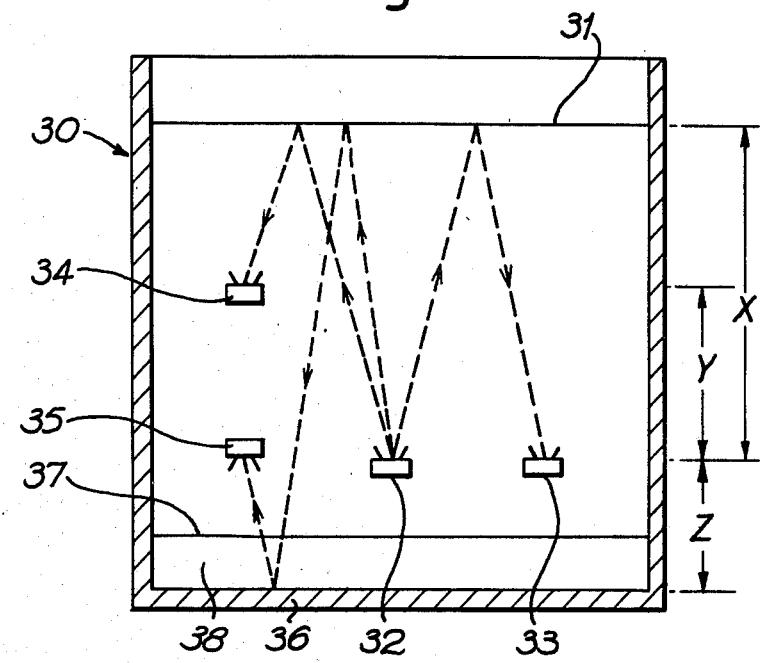

United States Patent [19]

Redding

[11] 4,364,273

[45] Dec. 21, 1982

[54] APPARATUS FOR LOCATING INTERFACES IN MEDIA

[76] Inventor: Robert J. Redding, September House, Cox Green La., Maidenhead, Berkshire, England, SL6 3EL

[21] Appl. No.: 195,404

[22] Filed: Oct. 9, 1980

[30] Foreign Application Priority Data

Feb. 15, 1980 [GB] United Kingdom ............... 8005149

[51] Int. Cl.³ .................. G01N 29/04; G01N 9/24; G01F 23/00; G01S 15/32
[52] U.S. Cl. ............................. 73/614; 73/611; 73/615; 73/619; 73/290 V; 128/660; 367/101
[58] Field of Search ............... 73/611, 618, 619, 620, 73/626, 290 V, 114, 115; 367/97, 101, 102; 343/7 PL; 128/660, 661, 662, 663

[56] References Cited

U.S. PATENT DOCUMENTS

| | | | |
|---|---|---|---|
| 2,769,158 | 10/1956 | Schultz | 367/101 |
| 3,184,969 | 5/1965 | Bolton | 73/290 V |
| 3,646,506 | 2/1972 | Suter | 367/97 |
| 3,649,123 | 3/1972 | Ulicki | 343/7 PL |
| 3,730,628 | 5/1973 | Wolcott et al. | 343/7 PL |
| 3,815,409 | 6/1974 | Macouski | 73/615 |
| 3,948,248 | 5/1976 | Zuckerman et al. | 128/660 |
| 4,122,427 | 10/1978 | Karsh | |
| 4,159,647 | 7/1979 | Paulsen et al. | 73/290 V |
| 4,167,879 | 9/1979 | Pedersen | |
| 4,197,856 | 4/1980 | Northrop | 128/660 |
| 4,200,921 | 4/1980 | Buckley | |
| 4,222,274 | 9/1980 | Johnson | 128/660 |
| 4,271,707 | 6/1981 | Lakin | 73/614 |

FOREIGN PATENT DOCUMENTS

55-125464 9/1980 Japan .................. 343/7 PL
2043899 10/1980 United Kingdom ........... 367/102

OTHER PUBLICATIONS

Ultrasonic Testing of Materials, 2nd Ed. by Krautkrämer et al., published 1977 by Springer-Verlag, pp. 176-178.
Measurements and Control, vol. 13, No. 1, Jan 1980, London, by R. J. Redding, "A New Genus of Transducer?" pp. 27-30.

Primary Examiner—Edward R. Kazenske
Assistant Examiner—David V. Carlson
Attorney, Agent, or Firm—Kemon & Estabrook

[57] ABSTRACT

Apparatus to detect and/or locate an inhomogeneity in a medium comprises a transducer to transmit frequency-modulated ultrasonic energy through the medium and a transducer to receive reflected energy. The transducers are connected to a phase-locked loop which maintains a required relationship between the phase of the transmitted modulation and the phase of the received modulation by adjustment of the modulation frequency. The modulation frequency adjustment is kept within predetermined upper and lower frequency limits so that the loop can lock only on to received ultrasonic energy which has travelled a distance within a predetermined region in the medium. The energy may be scanned across the region to produce a profile of the inhomogeneity, such as tissue at a certain depth within a limb.

9 Claims, 4 Drawing Figures

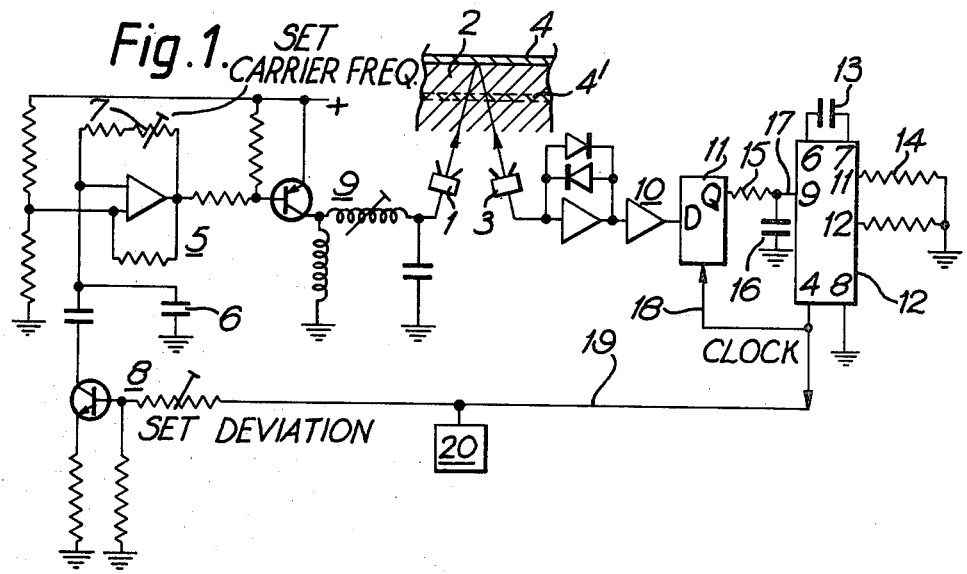
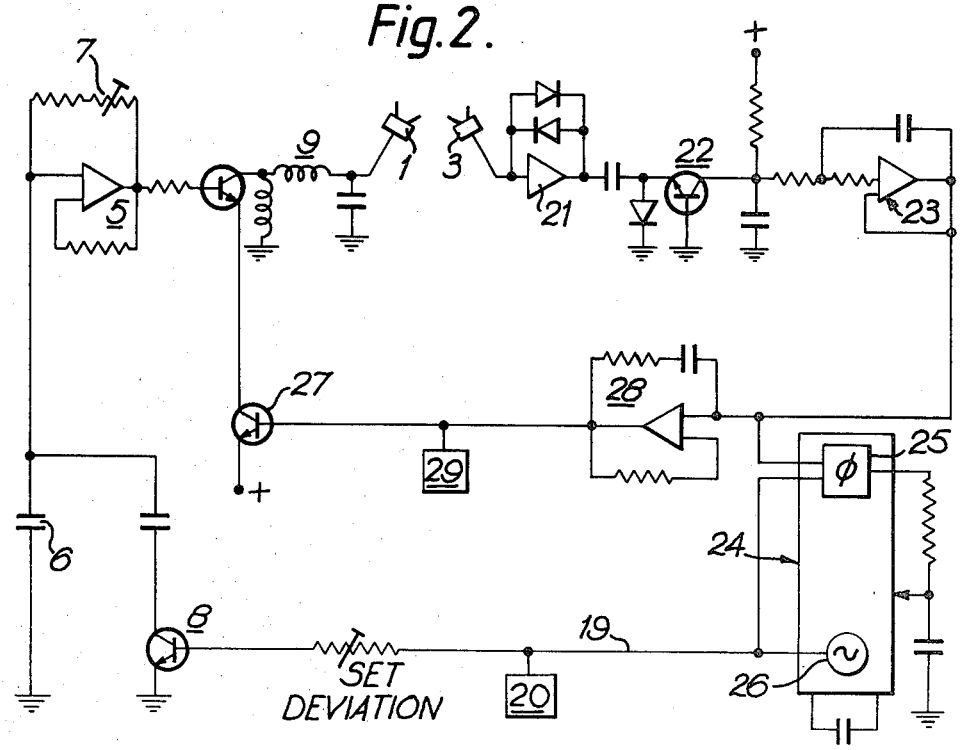

APPARATUS FOR LOCATING INTERFACES IN MEDIA

This invention relates to apparatus for detecting interfaces occurring in systems of solid and/or fluid media.

By use of the invention, images representing differences in consistency of the media for use, for example, in the detection of flaws in workpieces and in medical diagnosis, may be obtained. In known medical diagnosis methods, such as tomography, a beam of x-rays or ultrasound is obscured or reflected by variations in the medium. Nucleonic sources are sometimes used in the known scanning systems.

It is an object of the present invention to detect interfaces occurring in a medium by use of a benign ultrasonic beam, comprising a carrier wave which is frequency modulated. By controlling the carrier frequency and the modulating frequency, data relating to interfaces occurring within a given depth or thickness of a medium can be obtained. Hence, the presence of a change in tissue consistency, such as occurs when a cancerous growth is present, can be diagnosed without the danger and expense of complicated scanning systems using x-rays or nucleonic sources.

Other types of inhomogeneity can also be detected, such as strata occurring within a given depth of a liquid, or the presence of a layer of foreign material within, or at the boundary of, a liquid.

According to the present invention, apparatus to detect the presence of sound-reflective inhomogeneity in a selected region within a medium comprises a transducer to transmit frequency-modulated ultrasonic energy through the medium; a transducer to receive reflected ultrasonic energy; and means to adjust the frequency of the modulation to a valve within a predetermined range, the frequency limits of which depend upon the distances of the near and far boundaries, respectively, of the selected region from the transducers, to obtain a required relationship between the modulation phase of the transmitted ultrasonic energy and the modulation phase of the received energy only for a reflection from within said region.

Figure 4:
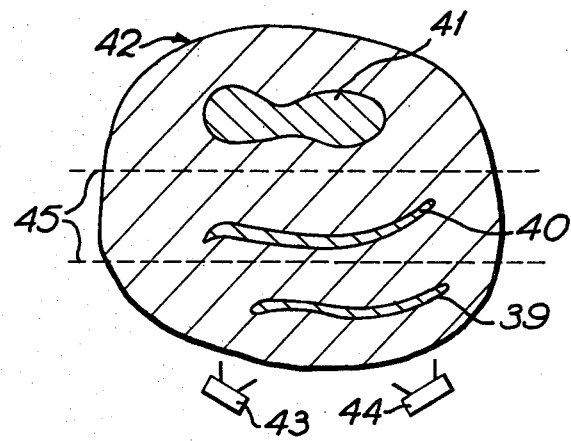

Embodiments of the invention will now be described, by way of example, with reference to the accompanying drawings, in which:

FIG. 1 is a schematic circuit diagram of one form of apparatus according to the invention, FIG. 2 is a schematic circuit diagram of another form of apparatus according to the invention, FIG. 3 shows schematically a cross-section through an oil tank incorporating apparatus according to the invention, and FIG. 4 illustrates the use of apparatus according to the invention for indicating the profiles of layers of different tissue or of bone within a limb.

Referring to FIG. 1 of the drawing, apparatus to detect the presence of inhomogeneity in a medium comprises an ultrasonic transducer 1 which is disposed to transmit ultrasonic energy into the medium, for example a liquid 2, and a transducer 3 which is disposed to receive ultrasonic energy reflected from an inhomogeneity represented by an interface 4 with some other material. The transducer 1 is energized by an oscillator 5 which produces a carrier signal, the center frequency of which is determined by a capacitor 6 and a variable resistor 7. The carrier signal is modulated by a frequency-modulation circuit 8, and the modulated carrier is fed to the transducer 1 via a power amplifier 9.

The receiving transducer 3 feeds the received frequency-modulated carrier signal to an amplifier-limiter and f.m. demodulator circuit 10. The demodulated output, i.e. the received modulation, is fed to D-type flip-flop 11 (e.g. type 4013) which is connected in a phase-locked loop with a P.L.L. integrated circuit 12. The circuit 12 may comprise any suitable chip (such as the 4046 chip) incorporating a voltage-controlled oscillator (VCO) and a phase comparator. A capacitor 13 and a resistor 14 are provided to determine the center operating frequency of the VCO. The output of the flip-flop 11 is fed, via a filter comprising a resistor 15 and a capacitor 16, to a control voltage input 17 of the circuit 12.

The VCO output is fed via a line 18 to a "clock" input of the flip-flop 11, and is also fed via a line 19 to the frequency-modulation circuit 8 as the modulation frequency. A frequency-dependent display 20 is connected to the line 19.

In describing the operation of the circuit, it will firstly be assumed that the interface 4 occurs at a distance from the transducers 1 and 3 which is within predetermined operating limits for the phase-locked loop circuit 12. The beam from the transducer 1 is reflected at the interface 4, and at least part of the energy is received at the transducer 3. The modulation fed to the flip-flop 11, together with the clock pulses on the line 18, cause the flip-flop to set and reset continuously, and the phase comparator of the PLL 12 compares the phase of the flip-flop output with the phase of the clock pulses and adjusts the modulation frequency accordingly if the correct phase relationship does not exist.

The relationship will be correct only if the path length travelled by the ultrasonic energy corresponds to an integral number of half-wave lengths of the modulation frequency. Hence, the modulation frequency gives a measure of the distance from the transducer 1 to the inhomogeneity 4. The display 20 therefore indicates that distance, either digitally or graphically.

If an inhomogeneity 4' now appears, energy from the beam will be reflected therefrom, and the phase-locked loop can adjust the modulation frequency to take into account the shorter distance travelled by the ultrasonic energy. The apparatus will, therefore, constantly monitor the existence of significant homogeneities, provided that the required modulation frequency falls within the working range of the phase-locked loop.

If the modulation frequency is forced to sweep over a wide range by sweeping the center frequency of the phase-locked loop, each time the frequency corresponds to the position of an inhomogeneity the loop will try to lock. Hence, the positions of all inhomogeneities within a given distance can be monitored.

Alternatively, if the loop operating frequency range is made narrow, only those inhomogeneities occurring within a given stratum of the medium will be taken into account. Hence, considering the inhomogeneities 4 and 4' in FIG. 1, the operating frequency range may be set so that the inhomogeneity 4 (for example the surface of a liquid) is ignored, but a dense layer of foreign body 4' present beneath the surface is located. Conversely, a layer 4' may be ignored and the layer 4 located by suitably setting the operating frequency range.

Various types of phase-locked loop circuits are known, and a particular type will be selected depending upon the required mode of operation. The circuit 12 in FIG. 1 is of the pulse-counting edge-controlled memory phase comparator type, and can be made very sensitive due to working on the leading edges of the modulation signal.

For higher stability, an exclusive-OR type of phase comparator may be used, which type considers only whole cycles of the modulation. A circuit including such a comparator and also including automatic power control will now be described, with reference to FIG. 2 of the drawings, in which components having the same functions as in the FIG. 1 circuit have the same reference numerals as in that figure. In this case, the output of the transducer 3 is fed to limiter-amplifier 21, and the received frequency-modulated carrier is then demodulated by a pulse-counting demodulator 22. The resultant modulation is fed via a constant-phase low-pass filter 23, for example of the Butterworth type, to a phase-locked loop (P.L.L.) integrated circuit 24, which may be a type 4046 chip as in the FIG. 1 embodiment, but using an exclusive-OR P.L.L. configuration 25 provided therein instead of the type of comparator circuit used in FIG. 1. One input to the circuit 25 comprises the received modulation, and the other input is provided by a voltage-controlled oscillator (V.C.O.) 26. The V.C.O. output provides the modulating signal, as previously described, and is fed to the display 20 and to the frequency-modulation circuit 8.

The loop gain of the FIGS. 1 and 2 circuits has no effect on the accuracy of the measurements over wide limits, but it can be controlled automatically to give a substantially constant received modulation signal, irrespective of changes in the attenuation of the path along which the ultrasonic energy is transmitted and received. This can be achieved, as shown in FIG. 2, by controlling the input power fed to the power amplifier 9 using a signal fed back from the amplifier 21 such as to ensure that the power is kept at a level for which the amplifier 21 just limits. The input power to the amplifier 9 is controlled by a transistor 27, and the feed back signal is derived by feeding the modulation output from the filter 23 through an integrator circuit 28 and thence to the base electrode of the transistor 27. The feedback signal provides a measure of the attenuation of the path via which the ultrasonic energy passes between the transducers 1 and 3, and this can be fed to an indicator or display 29. Changes in the displayed attenuation value could, for example, indicate the presence of bubbles or solid particles in a normally liquid medium.

Referring now to FIG. 3 of the drawings, a tank 30 contains oil up to a level 31. A transmitting transducer 32 located in the oil is connected to a circuit (not shown) such as described above and transmits frequency-modulated ultrasonic energy upwards through the oil. Energy reflected from the surface 31 is received by an upward-pointing receiving transducer 33 and, via a different path, by a second upward-pointing receiving transducer 34 a vertical distance Y above the transmitting transducer 32. A third receiving transducer 35 points downwards to receive energy reflected firstly by the surface 31 and then by the base 36 of the tank, or, as will be explained later, by the surface 37 of a layer of water or sediment 38. The transducers 32,33 and 35 are all located at a fixed distance Z above the base 36. The level 31 is at a variable distance X above the transducers 32, 33 and 35.

While the transmitting transducer 32 is permanently connected to the modulation and P.L.L. circuitry, the receiving transducers 33, 34 and 35 may be switched into circuit sequentially by electronic switching means (not shown) which also causes any necessary change in the modulation center frequency and the frequency range as each transducer is connected.

The frequency ($F_1$) for the transmission from the transducer 32 to the transducer 33 could be used to determine 2X, and hence the height of the surface 31 above the base 36 could be obtained. However, by taking another frequency setting ($F_2$) using the transducers 32 and 34, an indication of $2X-Y$ is obtained. Y is a known value, and the value of X can be obtained from $$X=(Y/2)\cdot F_1/(F_1-F_2).$$

This will take into account changes in the density of oil which may occur near the surface 31, and/or the production of vapour.

If a modulation frequency $F_3$ is produced for ultrasonic energy received by the transducer 35, it can readily be checked whether this frequency truly corresponds to the distance $2X+2Z$ i.e. that reflection of the energy has taken place at the surface 31 and at the base 36. For this frequency to be correct, $F_3-F_1$ should represent 2Z. If it is found that $F_3$ is not correct, it follows that there must be some inhomogeneity elsewhere, such as at the surface 37 of a layer 38 of water or sediment at the bottom of the tank. The value $F_3-F_1$ will give an indication of the location of the layer.

The weight of oil in the tank may be computed from the measured height of the level 31 and the temperature of the oil. If the speed of sound in the liquid at a given temperature in known, the average temperature of the liquid in the path followed by the ultrasonic energy can be computed from the resultant modulation frequency.

It will be seen that if the height of the oil level is known from use of some other measuring system, the ultrasonic apparatus can be used to give warning of the presence of an inhomogeneity beneath the surface. In this case, the operating frequency range is selected so that the apparatus will not take into account reflections from the surface.

In a tank containing liquid petroleum gas, such an inhomogeneity could be an unusually dense layer adjacent the surface, produced by local cooling following the drawing-off of some of the gas. Such a layer can be potentially highly dangerous, because it may suddenly sink to the bottom of the tank following a path round the periphery of the tank, accompanied by a general swirling of the contents of the tank. The forces produced may be large enough to overturn the tank, so it is extremely advantageous to be forewarned that a dense layer is beginning to form.

Referring now to FIG. 4 of the drawings, the apparatus can be used for investigating the profiles of various layers of tissue 39 and 40 and bone 41 within a limb 42. Transmitting and receiving transducers 43 and 44, respectively, are located adjacent the limb and are connected to a frequency modulation and P.L.L. circuit as described above.

By selection of the operating modulation frequency range, reflections from an interface in a particular stratum of the limb can be obtained and the location of the interface indicated in the manner described above. The transducers may be made to scan across the limb, so that the profile of the interface can be displayed on the unit 20.

For example, the stratum contained between dotted lines 45 in FIG. 4 may be investigated, and reflections will be obtained from the tissue 40. The profile of this tissue will be plotted as the transducers 43 and 44 scan the limb.

Due to the limited modulation frequency range, reflections from the tissue 39 will be ignored, as will those from the bone 41. If it is desired to investigate the tissue 39 or the bone 41, the frequency range must be adjusted accordingly.

The apparatus can be used for scanning articles such as metal castings. The presence of any inhomogeneity which will cause a change in the speed of sound in the article, and hence will cause reflection of the ultrasonic beam, can be detected. The position of impurities, cracks or blowholes can be determined from the resultant modulation frequency when the PLL has locked.

The apparatus may be used with gases, liquids or solids and will show the interface when a change of phase occurs. When dealing with a solid or animate material it may be advantageous to reduce the interface losses between the transducers and the object under test by means of a coupling fluid, as is well known in non-destructive testing practice. Alternatively, the object and the transducers can be immersed in a fluid, for example water, so that the energy is concentrated at the area of interest.

I claim:

1. Apparatus to detect the presence of a sound-reflective inhomogeneity in a selected region of a medium, the apparatus comprising means to generate a frequency-modulated electrical signal; a first ultrasonic transducer; means to feed said electrical signal to said first transducer to cause said first transducer to transmit frequency-modulated ultrasonic energy into the medium along a direction which crosses near and far limits of said region; a second ultrasonic transducer to receive ultrasonic energy reflected from within said medium; means to monitor the phase of the modulation of said transmitted ultrasonic energy and the phase of the modulation of said received ultrasonic energy; means to adjust the modulation frequency of said ultrasonic energy to obtain a required relationship between said transmitted and received modulation phases, said modulation frequency lying between first and second limiting frequencies which correspond, respectively, to the positions of said near and far limits of said region relative to said transducers, whereby said required phase relationship is obtainable only for reflections from within said selected region; and means responsive to said modulation frequency to display information relating to the presence of said inhomogeneity.

2. Apparatus as claimed in claim 1, wherein said means to adjust said modulation frequency comprises a phase-locked loop.

3. Apparatus as claimed in claim 1, including means to cause scanning of said frequency-modulated ultrasonic energy across said selected region to detect the profile of a said inhomogeneity present in said selected region.

4. Apparatus as claimed in claim 3, wherein said display means is responsive to successive modulation frequency values determined as said ultrasonic energy is scanned across said selected region, to display said profile.

5. Apparatus to detect the presence of a sound-reflective inhomogeneity in a selected region beneath the surface of a liquid, the apparatus comprising means to generate a frequency-modulated electrical signal; a first ultrasonic transducer located within the liquid; means to feed said electrical signal to said first transducer to cause said first transducer to transmit frequency-modulated ultrasonic energy through the liquid towards said surface along a direction which crosses near and far limits of said region; a second ultrasonic transducer located within the liquid to receive ultrasonic energy reflected within said liquid; means to monitor the phase of the modulation of said transmitted ultrasonic energy and the phase of the modulation of said received ultrasonic energy; means to adjust the modulation frequency of said ultrasonic energy to obtain a required relationship between said transmitted and received modulation phases, said modulation frequency lying between first and second limiting frequencies which correspond, respectively, to the positions of said near and far limits of said region relative to said transducers, whereby said required phase relationship is obtainable only for reflections from within said selected region; and means responsive to said modulation frequency to display information relating to the presence of said inhomogeneity.

6. Apparatus as claimed in claim 5, including a feedback loop to provide a signal for controlling the power level of said transmitted ultrasonic energy to maintain a substantially constant received ultrasonic energy level despite changes in attenuation due to the medium through which said ultrasonic energy passes between said transducers, said feedback loop signal then providing a measure of said attenuation.

7. Apparatus as claimed in claim 5, wherein said means to adjust said modulation frequency comprises a phase-locked loop.

8. Apparatus to detect the presence of a sound-reflective inhomogeneity in a liquid in a selected region adjacent the bottom of a container containing said liquid, said apparatus comprising means to generate a frequency-modulated electrical signal; a first ultrasonic transducer located within said liquid and facing said surface; means to feed said electrical signal to said first transducer to cause said first transducer to transmit frequency-modulated ultrasonic energy through the liquid towards said surface, whereby ultrasonic energy is reflected at said surface and travels downwards through said liquid along a direction which crosses near and far limits of said region; a second ultrasonic transducer located within said liquid and facing said bottom of said container to receive ultrasonic energy after successive reflections from said surface and said inhomogeneity; means to monitor the phase of the modulation of said transmitted ultrasonic energy and the phase of the modulation of said received ultrasonic energy; means to adjust the modulation frequency of said ultrasonic energy to obtain a required relationship between said transmitted and received modulation phases, said modulation frequency lying between first and second limiting frequencies which correspond, respectively, to the positions of said near and far limits of said region relative to the position of said transducers, whereby said required phase relationship is obtainable only for reflections from within said selected region; and means responsive to said modulation frequency to display information relating to the presence of said inhomogeneity.

9. Apparatus as claimed in claim 8, wherein said means to adjust said modulation frequency comprises a phase-locked loop.

* * * * *